(12) United States Patent
Wang et al.

(10) Patent No.: US 12,259,310 B2
(45) Date of Patent: Mar. 25, 2025

(54) BIOLOGICAL SAMPLE IMAGE COLLECTION DEVICE AND GENE SEQUENCER

(71) Applicant: BGI SHENZHEN, Shenzhen (CN)

(72) Inventors: Zhonghai Wang, Shenzhen (CN); Chutian Xing, Shenzhen (CN); Jianjun Jiang, Shenzhen (CN); Heming Jiang, Shenzhen (CN); Yongwei Zhang, Shenzhen (CN)

(73) Assignee: BGI SHENZHEN, Shenzhen (CN)

( * ) Notice: Subject to any disclaimer, the term of this patent is extended or adjusted under 35 U.S.C. 154(b) by 187 days.

(21) Appl. No.: 17/798,369

(22) PCT Filed: Jun. 10, 2020

(86) PCT No.: PCT/CN2020/095446
§ 371 (c)(1),
(2) Date: Aug. 9, 2022

(87) PCT Pub. No.: WO2021/248380
PCT Pub. Date: Dec. 16, 2021

(65) Prior Publication Data
US 2023/0113336 A1   Apr. 13, 2023

(51) Int. Cl.
*G01N 15/1434* (2024.01)
*G01N 21/64* (2006.01)

(52) U.S. Cl.
CPC ..... *G01N 15/1434* (2013.01); *G01N 21/6456* (2013.01); *G01N 2021/6478* (2013.01);
(Continued)

(58) Field of Classification Search
CPC ........... G01N 15/1434; G01N 21/6456; G01N 2021/6478; G01N 2201/0415;
(Continued)

(56) References Cited

U.S. PATENT DOCUMENTS

2003/0218730 A1   11/2003   Murakami et al.
2006/0057861 A1*   3/2006   Goto .................... G05B 19/402
                                                    438/800
(Continued)

FOREIGN PATENT DOCUMENTS

CN            1749901 A      3/2006
CN          105861293 A      8/2016
(Continued)

*Primary Examiner* — Christopher Wait
(74) *Attorney, Agent, or Firm* — ScienBiziP, P.C.

(57) ABSTRACT

A biological sample image collection device (100), comprising support (30) and an optical imaging assembly (50), also comprises: a plurality of movable platforms (40) for placing biological samples (20), wherein the plurality of movable platforms (40) are arranged on the support (30) in an array; the plurality of movable platforms (40) can move relative to the support (30); and forces acting on the support (30) during the movement of the movable platforms can cancel each other out, so as to avoid vibrations affecting the support (30) and the biological samples (20) are canceled. The optical imaging assembly (50) collects images of the biological samples (20) on the movable platforms (40) when the plurality of movable platforms (40) move, relative to the center of the array, in the same direction and at the same speed. Further provided is a gene sequencer including the biological sample image collection device (100).

17 Claims, 11 Drawing Sheets

(52) U.S. Cl.
CPC ............... *G01N 2201/0415* (2013.01); *G01N 2201/06113* (2013.01); *G01N 2201/0636* (2013.01); *G01N 2201/0638* (2013.01)

(58) Field of Classification Search
CPC . G01N 2201/06113; G01N 2201/0636; G01N 2201/0638; G01N 21/6428; G01N 21/6452; G01N 21/6458; C12M 41/36; C12Q 1/6869; G02B 21/16; G02B 21/18; G02B 21/361
See application file for complete search history.

(56) References Cited

U.S. PATENT DOCUMENTS

| | | |
|---|---|---|
| 2006/0110764 A1 | 5/2006 | Tang et al. |
| 2017/0022558 A1 | 1/2017 | Banyai et al. |

FOREIGN PATENT DOCUMENTS

| | | |
|---|---|---|
| EP | 0951054 A1 | 10/1999 |
| JP | S62035212 A | 2/1987 |
| JP | H05041194 A | 2/1993 |
| JP | H09090233 A | 4/1997 |
| JP | 2005032812 A | 2/2005 |
| JP | 2010276831 A | 12/2010 |
| JP | 2012042657 A | 3/2012 |

\* cited by examiner

BIOLOGICAL SAMPLE IMAGE COLLECTION DEVICE AND GENE SEQUENCER

FIELD

The present disclosure relates to technical field of biological sample information collection, especially relates to a biological sample image collection device and gene sequencer.

BACKGROUND

Devices for collecting information from biological samples, such as a gene sequencer, collect and image fluorescence emitted by a fluorescent group carried by a base in a biological sample (nucleic acid), the sample is placed on a platform in an optical system, so as to identify the base and complete the collection. With the development of optical technology, there are more and more requirements for information from the gene sequencer or other device handling the biological samples. In order to improve the information from the information collection device, a first method is to increase the field of vision of the optical system. A second method is to use a movable platform to increase the information by moving the sample being imaged. The faster the platform moves, the greater the amount of information can be obtained. The first method redesigns the existing optical system, but an optical system with large field of view has complex structure and high cost. In the second method, the faster the platform moves, the stronger will be the effect on the optical system. Vibration caused by the movement may cause the imaging quality of the optical system to decline. Therefore, the existing devices do not have simple structures in combination of high-quality images of the samples.

SUMMARY

It is necessary to provide a biological sample image collection device and gene sequencer which are simple in structure and can obtain high-quality images of biological samples.

A biological sample image collection device, which includes a support and an optical imaging assembly. The biological sample image collection device also includes:

a plurality of movable platforms which are movably connected to the support, the plurality of movable platforms are configured for placing biological samples and can be driven to move. The plurality of movable platforms is distributed to form an array on the support. The plurality of movable platforms can move relative to the support and the forces acting on the support during such movement are balanced in opposition and offset each other, to avoid vibration of the biological samples caused by the movement;

an optical imaging assembly, collecting images of biological samples on the movable platform when the plurality of movable platforms moves relative to the support platform.

In an embodiment of the present disclosure, the optical imaging assembly includes: a light source output device for outputting light; a first dichroic mirror for receiving and reflecting the light output by the light source output device; an objective lens, arranged above the movable platform, is configured to focus the light reflected by the first dichroic mirror onto the biological sample to excite a fluorescent marker in the biological sample to generate fluorescence, and the fluorescence is emitted and projected onto the first dichroic mirror; the first dichroic mirror is further configured for transmitting the florescence projected by the objective lens; an image sensor for sensing the received light to form an fluorescent image of the biological sample; and a light guide for guiding the fluorescence light transmitted by the first dichroic mirror to the image sensor.

In an embodiment of the present disclosure, the biological sample image collection device includes a plurality of objective lenses and one image sensor, a photosensitivity range of the image sensor is greater than a sum of imaging ranges of the plurality of objective lenses.

In an embodiment of the present disclosure, a plurality of objective lenses are arranged above each movable platform, distances between each objective lens is equal, and projections of the objective lens divide an image of the biological sample into a plurality of sub images with equal spacing.

In an embodiment of the present disclosure, the biological sample image collection device includes a plurality of objective lenses and a sample position exchange member. The focusing distances of all objective lenses are at different heights above the movable platform. Each objective lens is configured to focus light on a slide of a plurality of slides where the biological sample is on. When the plurality of movable platforms move relative to the support so that each of the plurality of objective lenses collect fluorescence from a respective one of the plurality of slides, the sample position exchange member changes position of the biological samples under the plurality of objective lenses.

In an embodiment of the present disclosure, the sample position exchange member is a rotating platform connected to the plurality of movable platforms. The plurality of movable platforms is movably connected to the rotating platform. The rotating platform is arranged on the support, and rotatable around a center of the array on a plane parallel to the movable platforms to exchange positions of the plurality of movable platforms.

In an embodiment of the present disclosure, the sample position exchange member includes a manipulator and a plurality of rotating platforms connected to the plurality of movable platforms. The manipulator places the biological samples from one movable platform to another movable platform. The plurality of movable platforms is movably connected to the plurality of rotating platforms. The plurality of rotating platforms can drive the biological samples to rotate on a plane parallel to the movable platform.

In an embodiment of the present disclosure, there is an even number of the movable platforms; all the movable platforms are arranged in a rectangle on the support. Each of the even number of movable platforms moves closer to or away from a symmetry axis of the rectangle simultaneously.

In an embodiment of the present disclosure, the plurality of movable platforms are equally spaced in a circle on the support, angles between two adjacent movable platforms are equal, and all of the movable platforms move closer to or away from a geometric center of the circle simultaneously.

A gene sequencer which includes the biological sample image collection device is also disclosed.

The plurality of movable platforms of the biological sample image collection device and the gene sequencer are distributed to form an array on the support, and the forces acting on the support offset each other when the plurality of movable platforms are moved, thus vibrations affecting the support and the stability of the biological samples are canceled, and the objective lens is thus able to obtain accurate fluorescence distribution, so as to form a high-quality fluorescence image of the biological sample using the image sensor for light sensing. Compared with the prior art, the biological sample image collection device has the advantages of simple structure and high-quality images of biological samples.

DESCRIPTION OF MAIN COMPONENTS OR ELEMENTS

Figure 1:
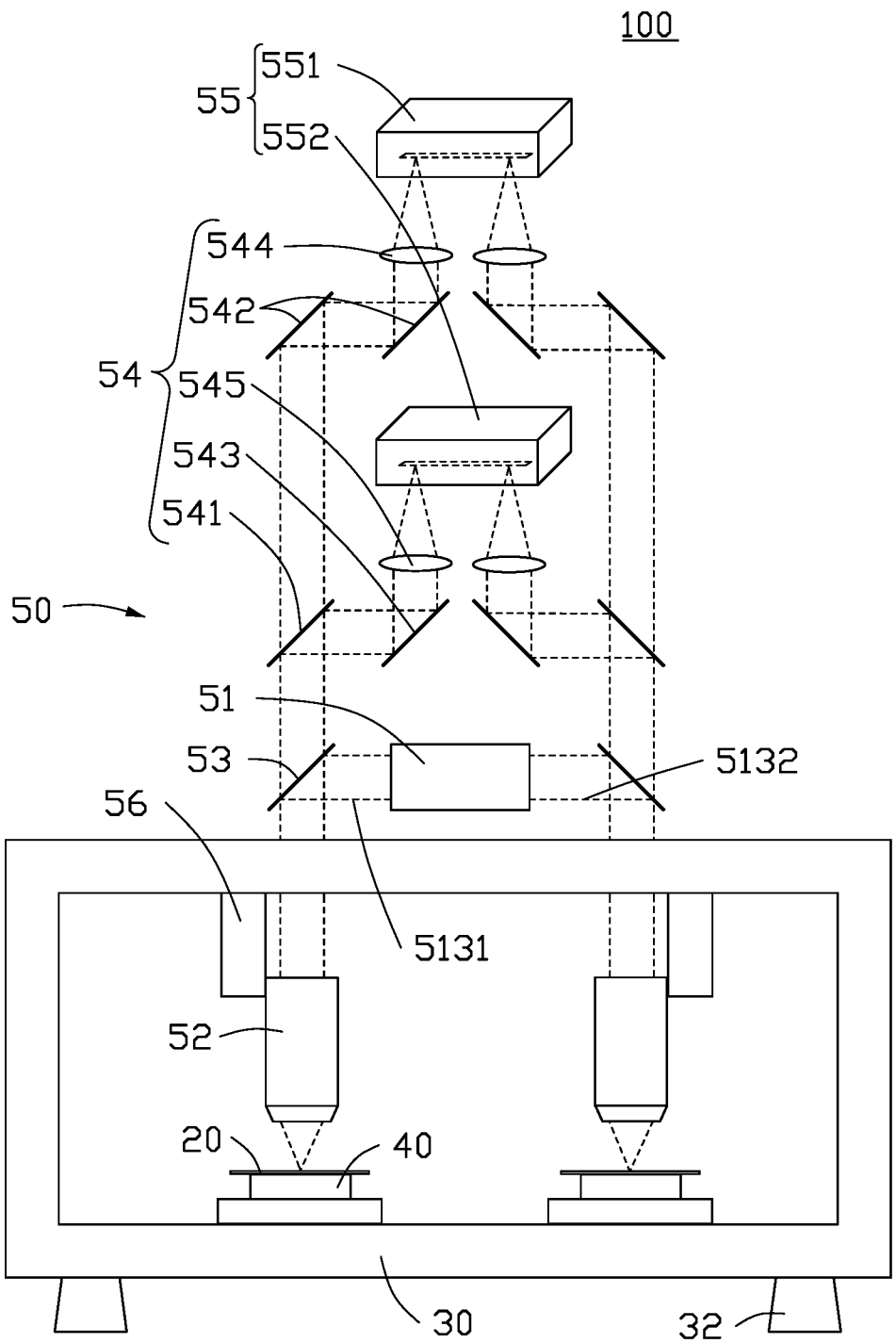
FIG. 1 is a schematic diagram of a biological sample image collection device in the first embodiment of the present disclosure.

Biological sample image collection device 100, 200, 300, 400;
Biological sample 20;
Support 30;
Damping pad 32;
Movable platform 40;
Optical imaging assembly 50;
Light source output device 51;
Laser transmitter 511, 515;
Collimating lens 512;
Splitting prism 513;
Laser-beam 5131, 5132;
Reflector 514;
Optical splitter 516;
Collimator 517;
Objective lens 52;
First dichroic mirror 53;
Light guide 54;
Second dichroic mirror 541;
First reflecting mirror 542;
Image sensor 55;
First image sensor 551;
Second image sensor 552;
Lifting member 56;
sample position exchange member 60;
Manipulator 62;
Rotating platform 64.

DETAILED DESCRIPTION

The present disclosure will be further described in detail below in combination with the accompanying drawings.

In order to better understand the above objects, features and advantages of the disclosure, the disclosure is described in detail below in combination with the accompanying drawings and embodiments. It should be noted that the embodiments and features in the embodiments of the present application can be combined with each other without conflict.

Many specific details are set forth in the following description to facilitate a full understanding of the disclosure. The described embodiments are only some of the embodiments of the disclosure, not all of them. Based on the embodiments of the disclosure, all other embodiments obtained by those skilled in the art without creative work belong to the protective scope of the disclosure.

Unless otherwise defined, all technical and scientific terms used herein have the same meanings generally understood by those skilled in the technical field of the present disclosure. The terms used in the specification of the disclosure herein are only for the purpose of describing specific embodiments, and are not intended to limit the disclosure.

Referring to FIG. 1, the present disclosure provides a biological sample image collection device 100 for acquiring an image of a biological sample 20.

The biological sample image collection device 100 includes a support 30, a plurality of movable platforms 40, and an optical imaging assembly 50. Multiple damping pads 32 are arranged at bottom of the support 30. The plurality of movable platforms 40 are movably connected to the support 30, and the plurality of movable platforms 40 are configured for placing biological samples 20 and driving the biological sample 20 to move. The plurality of movable platforms 40 are distributed on the support 30 in the form of an array. The plurality of movable platforms 40 can move relative to the support and the forces acting on the support 30 during the movement balance in opposition and so offset each other, so as to avoid vibration of the movement affecting the support 30 and the biological sample 20. Specifically, the plurality of movable platforms 40 counteract the forces acting on the support 30 during movement by moving in a same direction and at a same speed relative to an array center of the plurality of movable platforms 40. The same direction movement includes movement close to the array center and movement away from the array center. The optical imaging assembly 50 is arranged above the movable platforms 40, and the optical imaging assembly 50 is configured to collect images of biological samples 20 on the movable platforms 40 when the movable platforms 40 move relative to the array center.

The optical imaging assembly 50 includes a light source output device 51, an objective lens 52 placed above the movable platforms 40, a first dichroic mirror 53, a light guide 54, and an image sensor 55. The light source output device 51 is configured for outputting light. The first dichroic mirror 53 and the objective lens 52 are arranged one-to-one, and the first dichroic mirror 53 and the objective lens 52 are arranged between the objective lens 52 and the light source output device 51 to receive light output by the light source output device 51 and reflect the light onto the objective lens 52. The objective lens 52 is configured to focus the light reflected by the first dichroic mirror 53 on the biological sample 20 on the movable platform 40 to excite a fluorescent marker in the biological sample 20 to generate fluorescence, and emit and project the fluorescence to the first dichroic mirror 53 through the objective lens 52. In the embodiment of the present disclosure, the objective lens 52 is connected with a lifting member 56, the objective lens 52 can be moved up and down with the lifting member 56 to adjust a focusing position of the objective lens 52, to focus on the biological sample 20. The first dichroic mirror 53 is further configured to transmit the fluorescence projected by the objective lens 52 to the light guide 54. The light guide 54 and the first dichroic mirror 53 are arranged one-to-one, and the light guide 54 is configured to guide the light of fluorescence transmitted by the first dichroic mirror 53 to the image sensor 55. The image sensor 55 senses the received light to form a fluorescent image of the biological sample 20.

Referring to FIG. 1, the fluorescent markers in the biological sample 20 placed on the movable platform 40 generate different wavelengths of light under the excitation of specific wavelengths of light. The light guide 54 includes a second dichroic mirror 541, a first reflecting mirror 542, a second reflecting mirror 543, a first cylindrical lens 544, and a second cylindrical lens 545. The second dichroic mirror 541 receives the fluorescence transmitted by the first dichroic mirror 53, transmits a light of first wavelength in the fluorescence to the first reflecting mirror 542, and also reflects a light of second wavelength in the fluorescence to the second reflecting mirror 543. The first reflecting mirror 542 reflects light to the first cylindrical lens 544, and the second reflecting mirror 543 reflects light to the second cylindrical lens 545. In the embodiment of the present disclosure, there are two first reflecting mirrors 542, and there is one second reflecting mirror 543. In other embodiments, quantity of the first reflecting mirror 542 may be one or three or more, and quantity of the second reflecting mirror 543 may be two or more. Quantities of the first reflecting mirror 542 and the second reflecting mirror 543 are specifically determined according to relative positions between the first cylindrical lens 544 and the second dichroic mirror 541, and the second cylindrical lens 545 and the second dichroic mirror 541. The first cylindrical lens 544 and the second cylindrical lens 545 converge received light to the image sensor 55. The image sensor 55 senses lights of the first cylindrical lens 544 and the second cylindrical lens 545 to form a fluorescent image of the biological sample 20. In the embodiment of the present disclosure, the image sensor 55 includes a first image sensor 551 and a second image sensor 552. The first image sensor 551 receives the light converged by the first cylindrical lens 544 to form a first sample image. The second image sensor 552 receives the light converged by the second cylindrical lens 545 to form a second sample image.

In another embodiment, the fluorescent marker in the biological sample 20 placed on the movable platform 40 generates fluorescence under excitation by light. The light guide 54 differs from the light guide 54 shown in FIG. 1 in that the light guide 54 of the other embodiment includes a first reflecting mirror 542, but does not include the second dichroic mirror 541. The first reflecting mirror 542 directly receives the fluorescence transmitted by the first dichroic mirror 53 and transmits the fluorescence to the image sensor 55. Correspondingly, the image sensor 55 includes a first image sensor 551, but does not include a second image sensor 552.

Referring to FIG. 1, the biological sample image collection device 100 includes two movable platforms 40, each movable platform 40 carries one biological sample 20, and the biological sample image collection device 100 is configured to obtain images of the two biological samples 20.

Figure 2:
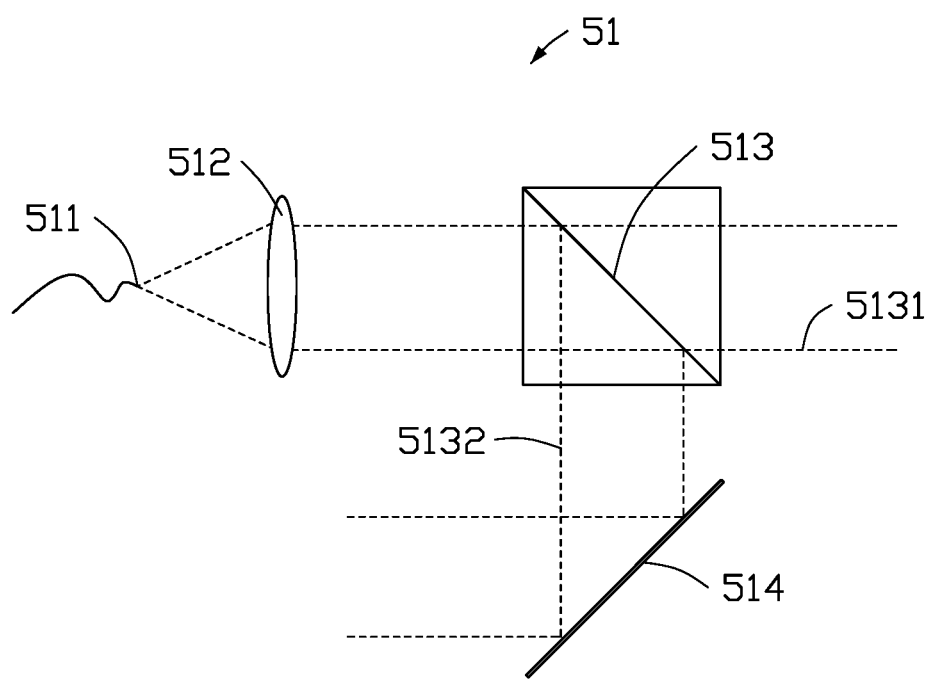
FIG. 2 is a schematic diagram of a light source output device in the collection device in FIG. 1.

The biological sample image collection device 100 includes two objective lenses 52, two first dichroic mirrors 53, two light guides 54 and the image sensor 55 arranged above the two movable platforms 40. The light source output device 51 is configured to output light to the two first dichroic mirrors 53. Specifically, as shown in FIG. 2, the light source output device 51 is placed between two first dichroic mirrors 53, the light source device 51 includes a laser transmitter 511, a collimating lens 512, a splitting prism 513, and a reflector 514. The laser transmitter 511 is configured for outputting laser (or "excitation light"). The collimating lens 512 is configured to collimate the laser and transmit the laser to the splitting prism 513. The splitting prism 513 divides the laser into two laser-beams 5131 and 5132. One laser-beam 5131 is reflected to one of the first dichroic mirrors 53 through the reflector 514, and other laser-beam 5132 is directly transmitted to the other of the first dichroic mirrors 53 after passing through the splitting prism 513, so that the laser output by the light source output device 51 is emitted to the two first dichroic mirrors 53. The splitting prism 513 can be a 50/50 splitting prism 513, and the 50/50 splitting prism 513 divides the laser into two laser-beams 5131 and 5132 with equal power. The two first dichroic mirrors 53 reflect the light output from the light source output device 51 onto the two objective lenses 52, and transmit the fluorescence excited from the two biological samples 20 projected by the two objective lenses 52 to the two light guides 54. The image sensor 55 is placed between the two first dichroic mirrors 53, to receive light introduced by the two light guides 54, to form a fluorescent image of the two biological samples 20. The photosensitivity range of the image sensor 55 is greater than a sum of imaging ranges of the two objective lenses 52, so that images of the two biological samples 20 can be formed on the same image sensor 55. In another embodiment, the photosensitivity range of the image sensor 55 is the same as the imaging range of one objective lens 52, and the biological sample image collection device 100 includes two image sensors 55 with the same number as the objective lens 52, each of the image sensor 55 forms a fluorescent image of the biological sample 20.

Figure 3:
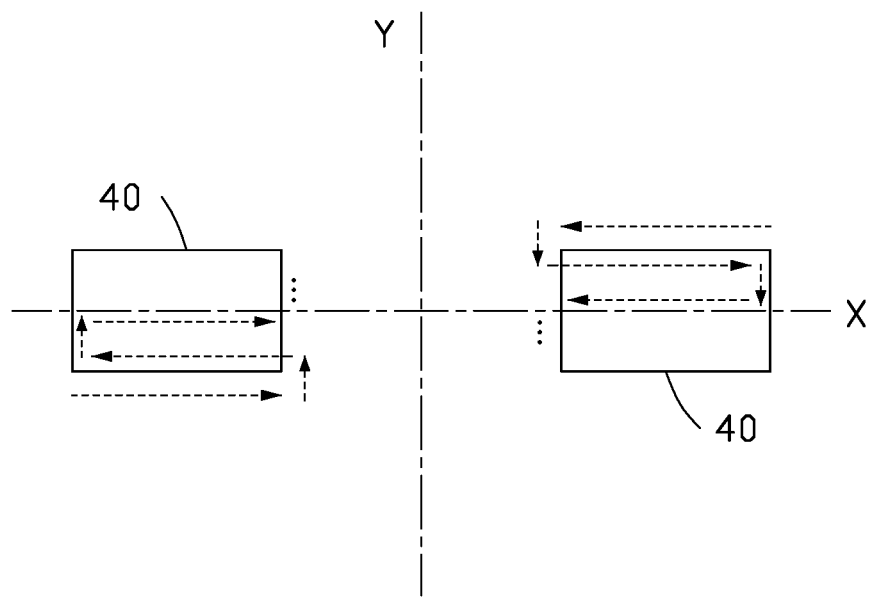
FIG. 3 is a schematic diagram of movement of a movable platform in the collection device in FIG. 1.

FIG. 3 shows that the two movable platforms 40 are positioned symmetrically along a first axis X and a second axis Y perpendicular to the first axis X, and the array center is the intersection of the first axis X and the second axis Y. The image sensor 55 may be a linear array camera, a TDI (time delay integration) camera, or an area array camera. The two movable platforms 40 can move parallel to the direction of the first axis X and parallel to the direction of the second axis Y. When the biological sample image collection device 100 collects the image of the biological sample 20, the two movable platforms 40 move parallel to the first axis X and relative to the array center oppositely and symmetrically at a same speed, and the two movable platforms 40 move from a first edge of the two biological samples 20 to a second edge of the two biological samples 20, the first edge is opposite to the second edge, so that the two objective lenses 52 can acquire fluorescence of a row parallel to the first axis X excited on the biological samples 20. Then, the two movable platforms 40 move parallel to the second axis Y relative to the array center oppositely and symmetrically at a same speed, and the two movable platforms 40 move to an end corresponding to the second edge on other row parallel to the first axis X on the two biological samples 20, and then the two movable platforms 40 move along the first axis X to an end corresponding to the first edge on the other row, so that the two objective lenses 52 can obtain fluorescence of the other row parallel to the first axis X excited on the biological samples 20. In this way, the two objective lenses 52 can acquire all the fluorescence on the biological sample 20 by scanning the biological sample 20 line by line. The multiple lines of fluorescence obtained by each objective lens 52 are transmitted to the image sensor 55 through the corresponding first dichroic mirror 53 and the light guide 54 to form a fluorescent image of the biological sample 20. In another embodiment, the two movable platforms 40 move from the first edge to the second edge of the biological sample 20, and the two movable platforms 40 move parallel to the first axis X, the two objective lenses 52 obtain fluorescence of a row parallel to the first axis X. The two movable platforms 40 return to the first edge of the two biological samples 20 along the first axis X. Then the two movable platforms 40 move parallel to the second axis Y relative to the array center at a same speed, and move to the end corresponding to the first edge on the other row parallel to the first axis X on the two biological samples 20. Then the two movable platforms 40 move along the first axis X to the end corresponding to the second edge on the other row, so that the two objective lenses 52 acquire the fluorescence of the other row excited on the biological sample 20 parallel to the first axis X. In this way, the two objective lenses 52 acquire images of all fluorescence on the biological sample 20 by scanning the biological sample 20 line by line. The scanning method of the biological sample 20 can also be other method. For example, the two movable platforms 40 may move from the center of the two biological samples 20, and the two biological samples 20 can be scanned line by line to obtain all the fluorescence on the two biological samples 20. The specific scanning method is determined according to need and design, which is not listed here. The two movable platforms 40 can move closer to or away from the array center when moving along the first axis X, and the two movable platforms 40 can also move closer to or away from the array center when moving along the second axis Y, which is determined according to initial positions of the two objective lenses 52 and the biological samples 20. During collection of images of the two biological samples 20, the two movable platforms 40 move relative to the array center in a same direction and at a same speed, and forces acting on the support 30 during the movement offset each other, so as to avoid vibration of the support 30 and the biological sample 20 placed the movable platform 40. Therefore, the objective lens 52 can obtain accurate image of distribution of fluorescence, so that the image sensor 55 can form high-quality images of the biological samples 20.

In another embodiment, a width of an area on the biological sample 20 where image needs to be collected is within a field of view of the objective lens 52. The image sensor 55 is a linear array camera, a TDI (time delay integration) camera, or an area array camera. The difference between the two movable platforms 40 of the other embodiment and the two movable platforms 40 shown in FIG. 3 is that the two movable platforms 40 of the other embodiment can move in a direction parallel to the first axis X, but not in a direction parallel to the second axis Y. When the biological sample image collection device 100 collects the image of the biological samples 20, the two movable platforms 40 move from two deviated edges of the two biological samples 20, parallel to the first axis X, to the other edge of the two biological samples 20 in a same direction and at a same speed relative to the array center, so that the two objective lenses 52 can obtain fluorescence of rows excited on the biological samples 20 parallel to the first axis X, so as to obtain fluorescence of the area to be imaged on the biological samples 20. The fluorescence obtained by each objective lens 52 is transmitted to the image sensor 55 through the corresponding first dichroic mirror 53 and the light guide 54 to form fluorescent images of the biological samples 20.

Figure 4:
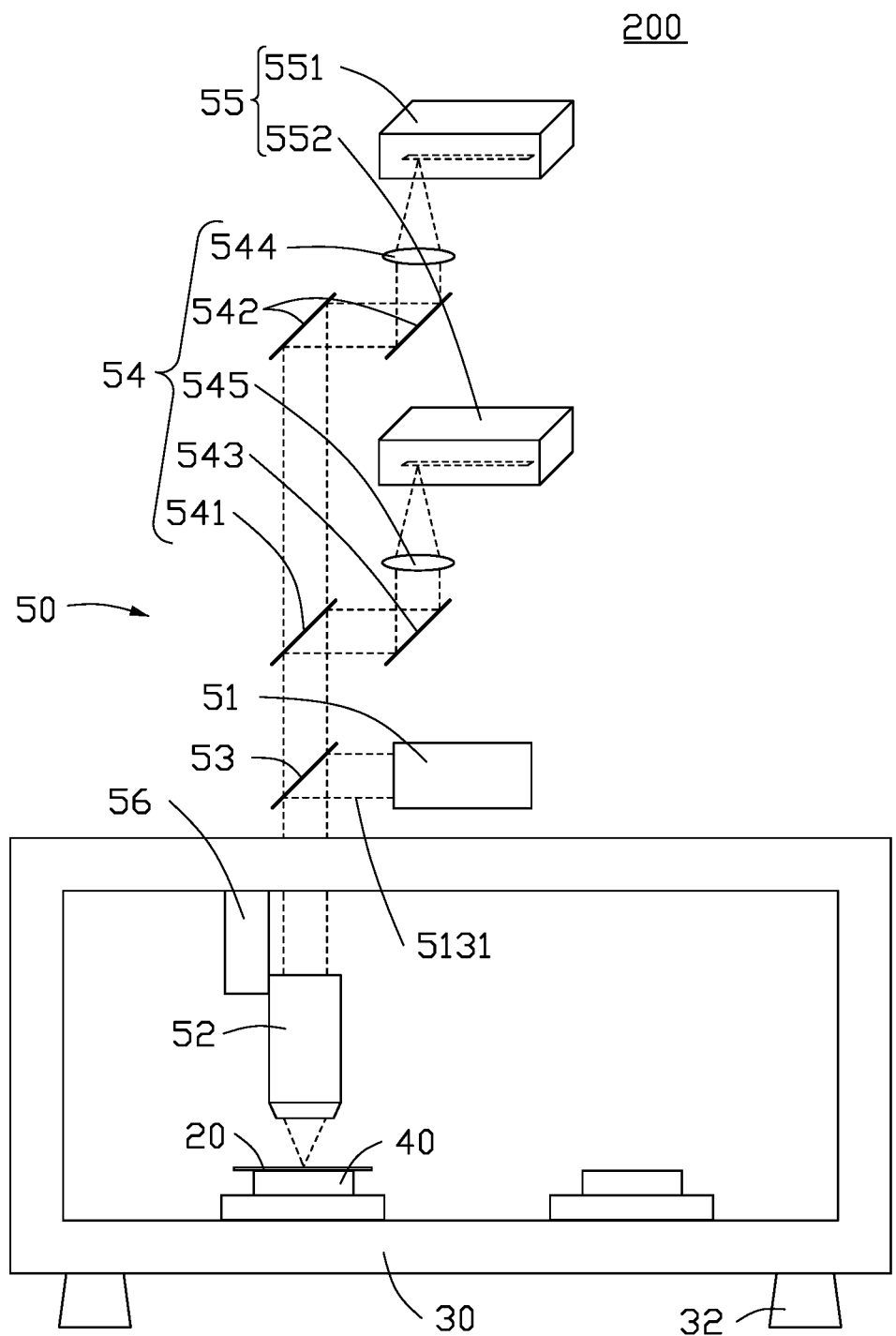
FIG. 4 is a schematic diagram of a biological sample image collection device in another embodiment of the present disclosure.

Referring to FIG. 4, FIG. 4 is a schematic diagram of the biological sample image collection device 200 provided in another embodiment. The difference between the biological sample image collection device 200 and the biological sample image collection device 100 shown in FIG. 1 is that the biological sample image collection device 200 includes two movable platforms 40, one of the movable platform 40 is provided with an objective lens 52 above the movable platform 40, and the other is not. Accordingly, the biological sample image collection device 200 only includes one first dichroic mirror 53 and one light guide 54 corresponding to the objective lens 52. The biological sample image collection device 200 is configured to acquire image of the biological sample 20 on the movable platform 40 provided with the objective lens 52 above. The process of the biological sample image collection device 200 acquiring image of the biological sample 20 is the same as that of the biological sample image collection device 100. During the acquisition process, the two movable platforms 40 move simultaneously, so as to avoid vibration of the support 30 and the biological sample 20 caused by the movement of the movable platform 40 under the objective lens 52, so as to obtain a high-quality image of the biological sample 20.

Figure 5A:
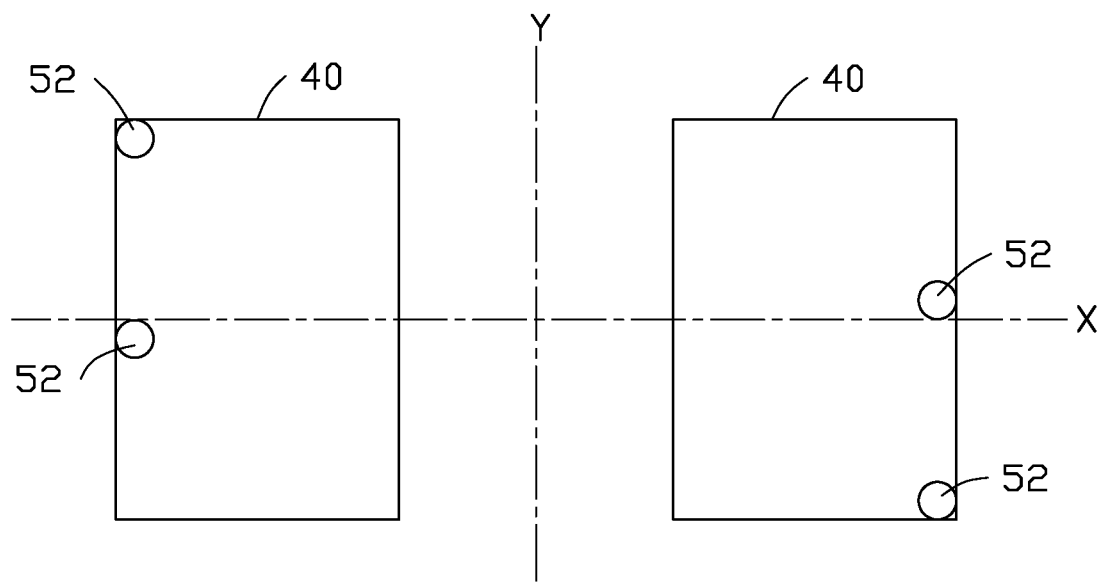
FIG. 5A is a schematic diagram of the movable platform corresponding to a plurality of objective lenses in an embodiment of the present disclosure.
Figure 5B:
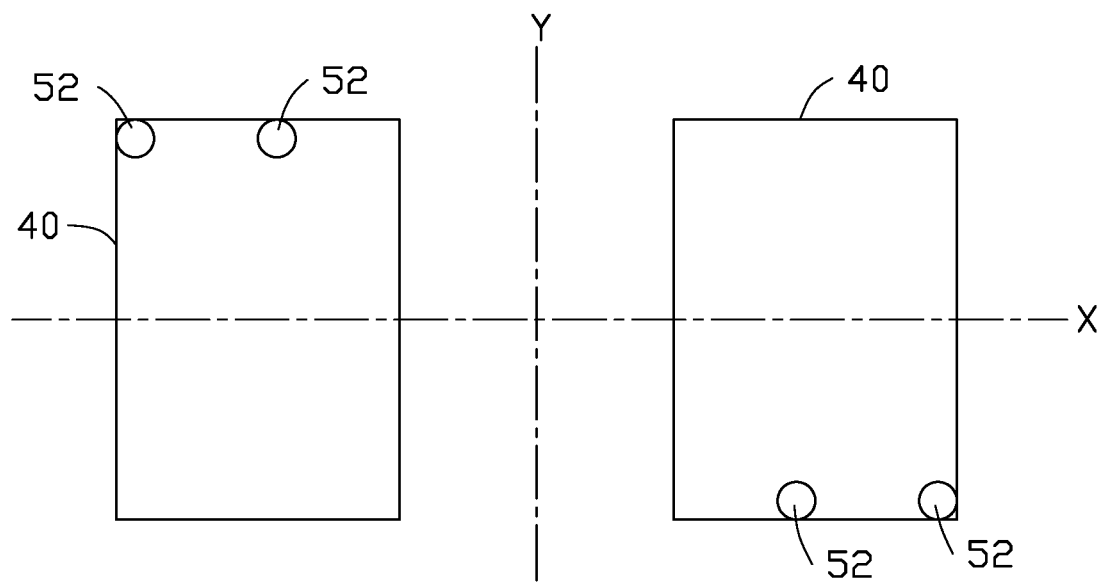
FIG. 5B is a schematic diagram of the movable platform corresponding to a plurality of objective lenses in another embodiment of the present disclosure.

Referring to FIG. 5A and FIG. 5B, in another embodiment, the objective lens 52 in the biological sample image collection device 100 of FIG. 1 is different in that two objective lenses 52 of the other embodiment are arranged above each movable platform 40. Distance between the two objective lenses 52 is half a length or width of the biological sample 20, and one of the objective lenses 52 is facing an edge of the biological sample 20. FIG. 5A shows that the distance between the two objective lenses 52 is half of the length of the biological sample 20, and FIG. 5B shows that the distance between the two objective lenses 52 is half of the width of the biological sample 20. The two objective lenses 52 on one of the movable platforms 40 and the two objective lenses 52 on the other movable platform 40 are centered on the array center. Thus, when the movable platform 40 travels for half the length or width of the biological sample 20 along the first axis X or the second axis Y, the two objective lenses 52 corresponding to each movable platform 40 can obtain fluorescence excited from the biological sample 20, so as to obtain image of the whole biological sample 20. In another embodiment, three, four or more objective lenses 52 may be arranged above each of the movable platforms 40, spacing distances between the objective lenses 52 are equal, and projections of the objective lenses 52 divide the biological sample 20 into a plurality of equally-spaced parts. The plurality of objective lenses 52 on one movable platform 40 and the plurality of objective lenses 52 on the other movable platform 40 are centered on the array center. Thus, when the movable platform 40 travels one third, one quarter, or less of the length or width of the biological sample 20 along the first axis X or the second axis Y, three, four, or more objective lenses 52 corresponding to each movable platform 40 can obtain fluorescence excited from the biological sample 20, so as to obtain image of the whole biological sample 20.

Figure 6:
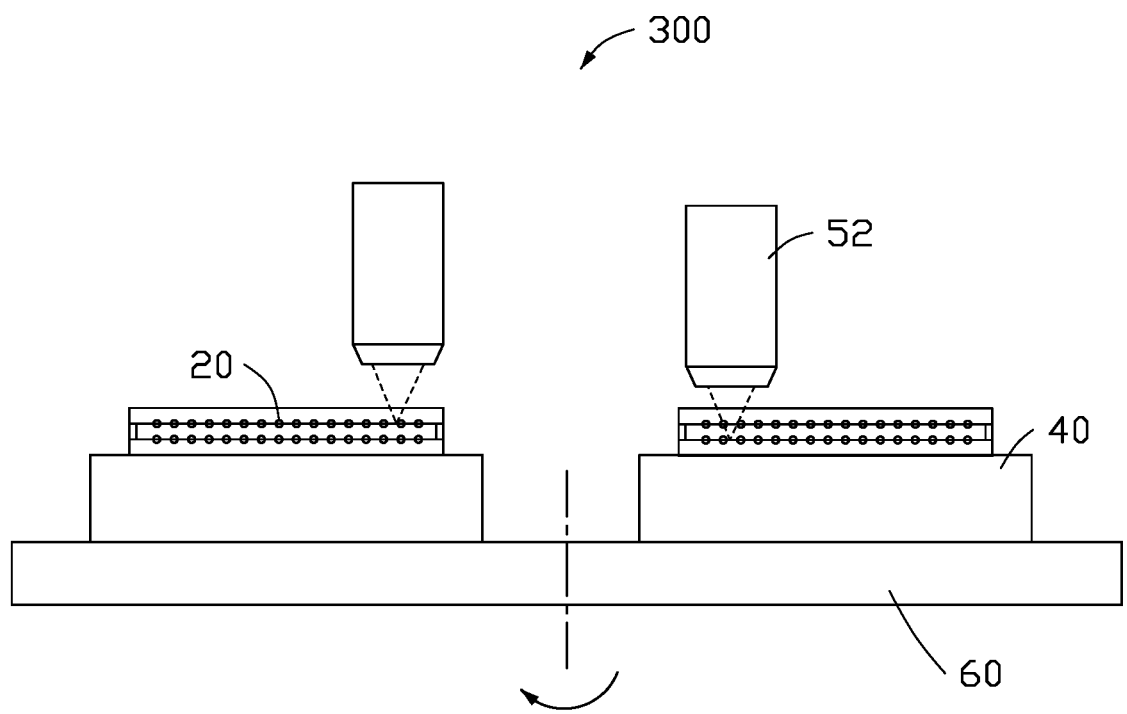
FIG. 6 is a schematic diagram of part of the biological sample image collection device in FIG. 1 when the biological sample is a double-layer slide.
Figure 7:
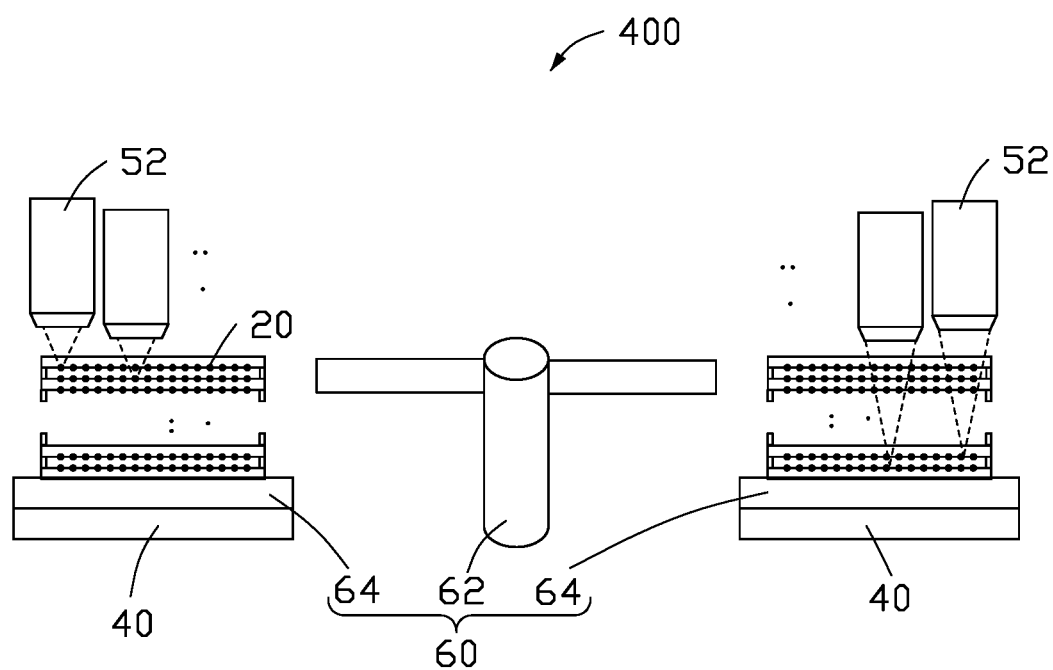
FIG. 7 is a schematic diagram of part of the biological sample image collection device in FIG. 1 when the biological sample is a multi-layer slide.

Referring to FIG. 6, FIG. 6 is a schematic diagram of a biological sample image collection device 300 provided in another embodiment. The biological sample image collection device 300 is similar to the biological sample image collection device 100 in FIG. 1. The differences between the biological sample image collection device 300 and the biological sample image collection device 100 are shown in FIG. 6. The difference between the biological sample image collection device 300 and the biological sample image collection device 100 is that the biological sample image collection device 300 also includes a sample position exchange member 60, and points of focus of the two objective lenses 52 placed above the two movable platforms 40 are located at different heights above the two movable platforms 40. The two objective lenses 52 are configured to focus light on slides of different layers on the biological sample 20 of double-layer slides, so as to excite fluorescent markers on slides at different heights to produce fluorescence, so that the two objective lenses 52 can collect fluorescence on different slides. When the two movable platforms 40 move in a same direction and at a same speed relative to the array center to enable the two objective lenses 52 to collect fluorescence on the same slide, the sample position exchange member 60 exchanges the positions of the two biological samples 20 under the two objective lenses 52. After exchanging positions of the two biological samples 20, the two movable platforms 40 move at a same speed relative to the array center again, so that the two objective lenses 52 can collect fluorescence on the other slide. In this way, fluorescence on the biological samples 20 of double-layer slide is collected through the two objective lenses 52, so that the image sensor 55 can obtain the fluorescence images of the biological samples 20. The sample position exchange member 60 shown in FIG. 6 is a rotating platform connected with the two movable platforms 40. The two movable platforms 40 are movably connected to the rotating platform, and the rotating platform is rotatably arranged on the support 30. The two movable platforms 40 can be rotated 180 degrees around the array center on a plane parallel to the movable platform 40, so that positions of the two biological samples 20 relative to the two objective lenses 52 can be interchanged. Referring to FIG. 7, in another embodiment, a sample position exchange member 60 in the biological sample image collection device 400 includes a manipulator 62, the manipulator 62 move the biological sample 20 located on one movable platform 40 to another movable platform 40 to exchange the positions of the two biological samples 20. Furthermore, considering that the positions of the biological samples 20 exchanged by the manipulator 62 are different from original positions of the biological samples 20, the sample position exchange member 60 further includes two rotating platforms 64 respectively connected with the two movable platforms 40. The rotating platforms 64 can drive the biological samples 20 to rotate on a plane parallel to the movable platform 40, so as to adjust positions of the two biological samples 20 to match positions of the two objective lenses 52, thus the two objective lenses 52 can collect fluorescence excited from the biological samples 20. In the embodiment shown in FIG. 7, two rotating platforms 64 are respectively placed on sides of the movable platforms 40 away from the support 30, and the biological samples 20 are placed on the rotating platforms 64. In another embodiment, the two rotating platforms 64 are respectively placed under the movable platforms 40, and the two rotating platforms 64 are positioned between the movable platform 40 and the support 30, the biological samples 20 are placed on the movable platforms 40.

FIG. 7 is a schematic diagram of the biological sample image collection device 400 provided in another embodiment. The biological sample image collection device 400 is similar to the biological sample image collection device 300 in FIG. 6. Differences between the biological sample image collection device 400 and the biological sample image collection device 300 are shown in FIG. 7. The differences are that quantity of objective lenses 52 arranged above the two movable platforms 40 is greater than two, and this number is equal to quantity of layers of a single slide in the biological samples 20. The points of focus of all objective lenses 52 above the two movable platforms 40 are located at different heights above the movable platform 40. Each objective lens 52 is configured to focus on a different layer of a slide of the biological sample 20, fluorescent markers of the biological sample 20 located on different layers of each slide can be excited to generate fluorescence, so that different objective lenses 52 collect fluorescence from different slides. In another embodiment, the quantity of objective lenses 52 above each movable platform 40 may be equal. The quantity of objective lenses 52 above one movable platform 40 may be two as shown in FIG. 5A or FIG. 5B. In other embodiments, quantity of objective lenses 52 above one movable platform 40 may also be three, four, or more. The quantity of objective lenses 52 above each movable platform 40 may also be different. For example, one objective lens 52 may be positioned above one movable platform 40, and two objective lenses 52 may be positioned above the other movable platform 40. A height of a point of focus of the objective lens 52 above one movable platform 40 may be greater than that of the objective lens 52 above the other movable platform 40. As shown in FIG. 6, heights of points of focus of the left multiple objective lenses 52 are greater than those of the right multiple objective lenses 52. In another embodiment, the heights of the focusing points of the left multiple objective lenses 52 may also be partially greater than that of the right objective lenses 52, and partially less than that of the right objective lenses 52. This ensures that the biological sample 20 on each layer of the slide is imaged by the corresponding objective lens 52. When the two movable platforms 40 move at a same speed relative to the array center to let the objective lenses 52 collect fluorescence on respective slides, the sample position exchange member 60 exchanges positions of the two biological samples 20 under the objective lens 52. The sample position exchange member 60 shown in FIG. 7 includes the manipulator 62 and the two rotating platforms 64. The sample position exchange member 60 can also be the rotating platform in FIG. 6. After exchanging the positions of the two biological samples 20, the two movable platforms 40 move in a same direction and at a same speed relative to the array center again, so that the objective lenses 52 above the movable platforms 40 collect fluorescence on remaining slides of the biological samples 20. In this way, fluorescence on multilayer slides is imaged through a plurality of objective lenses 52, and the image sensor 55 can obtain fluorescence images of the biological samples 20.

Figure 8:
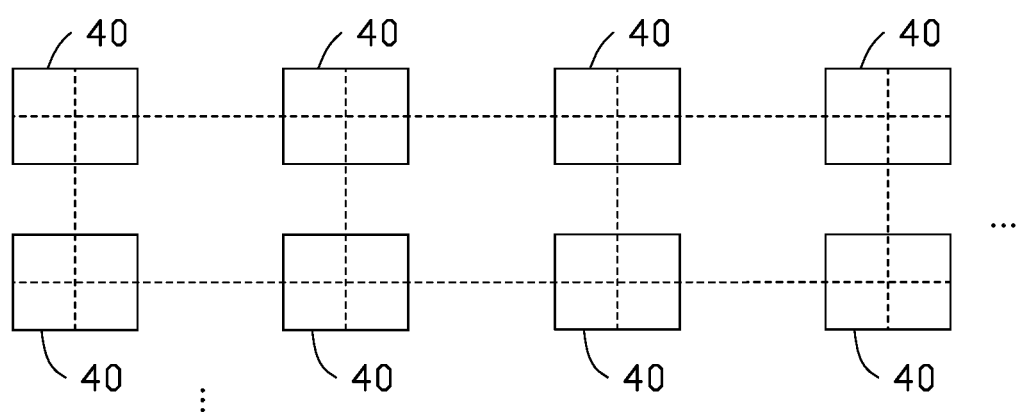
FIG. 8 is a schematic diagram of an arrangement of the movable platforms in another embodiment of the present disclosure.
Figure 9:
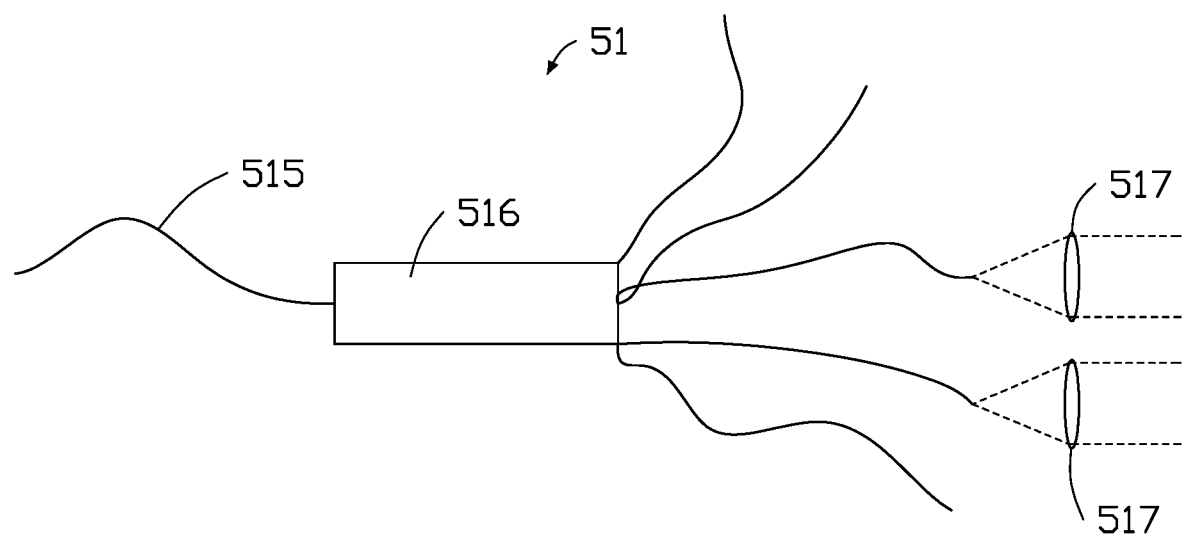
FIG. 9 is a schematic diagram of a light source output device matched with the movable platforms of the present disclosure.

FIG. 8 shows an arrangement of movable platforms 40 in another embodiment. In this embodiment, quantity of movable platforms 40 is an even number greater than two. All movable platforms 40 are arranged in a rectangle on the support 30, and the array center is a geometric center of the rectangle. Referring to FIG. 9, the light source output device 51 outputs an even number of light beams greater than two. The light beams are projected on the first dichroic mirror 53 corresponding to each movable platform 40 one-to-one, and are focused by the objective lens 52 to excite fluorescence from the biological sample 20 on each movable platform 40. The light source output device 51 includes a laser transmitter 515, an optical splitter 516, and a plurality of collimators 517. The laser transmitter 515 outputs a laser light, the optical splitter 516 includes a laser inlet and a plurality of laser outlets. The optical splitter 516 divides the laser input from the laser inlet into a plurality of laser beams of equal power, and the plurality of laser beams are output from a plurality of laser outlets respectively. Quantity of collimators 517 is the same as quantity of objective lenses 52. Collimators 517 are configured to collimate laser light output from a plurality of laser outlets into parallel light beams, and project the parallel light beams onto a plurality of first dichroic mirrors 53, and the first dichroic mirrors 53 project the parallel light beams onto a plurality of objective lenses 52. The light source output device 51 may further include a plurality of reflectors (not shown in the figures), the reflectors are configured for guiding the parallel light beams output by the collimator 517 onto the first dichroic mirrors 53 according to positions of the first dichroic mirrors 53. During collection of the image of the biological samples 20, all the movable platforms 40 are closer to or away from two symmetry axes of the rectangle, such as the first axis X and the second axis Y in FIG. 8, so that the objective lenses 52 located above the movable platforms 40 can collect fluorescence, and light is introduced into the image sensor 55 through the first dichroic mirrors 53 and the light guides 54 to record fluorescent images of a plurality of biological samples 20. Since the even number of movable platforms 40 move closer to or away from the symmetry axis of the rectangle, during the movement, forces acting on the movable platforms 40 and the support 30 offset each other, to avoid the vibration of the whole support 30 and of the biological sample 20 placed on the movable platform 40. The objective lenses 52 can obtain an accurate image of distribution of fluorescence, and the image sensor 55 can form high-quality fluorescence images of the biological samples 20.

Figure 10:
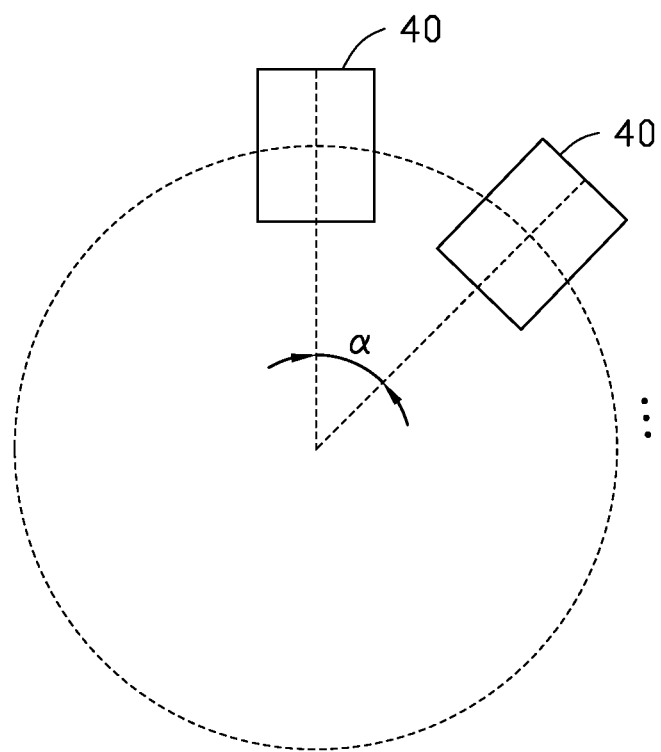
FIG. 10 is a schematic diagram of an arrangement of the movable platforms in another embodiment of the present disclosure.

FIG. 10 is an arrangement of the movable platforms 40 in another embodiment. In this embodiment, a plurality of the movable platforms 40 are equally spaced in a circle on the support 30, and an angle α exists between each adjacent movable platform 40. The array center is a center of the circle. During collection of the images of the biological samples 20, all the movable platforms 40 move closer to or away from the center of the circle to allow collection of fluorescence by the objective lens 52 located above the movable platform 40, and light is transmitted into the image sensor 55 through the first dichroic mirror 53 and the light guide 54 to record images of fluorescence of a plurality of biological samples 20. Since a plurality of movable platforms 40 moves closer to or away from the center of the circle, during the movement, forces acting on the movable platforms 40 and the support 30 offset each other, so as to avoid the vibration of the whole support 30 and the biological sample 20 placed on the movable platform 40, the objective lens 52 can obtain accurate fluorescence distribution, the image sensor 55 can form high-quality fluorescence images of the biological samples 20.

The movable platforms 40 of FIG. 8 and FIG. 10 may also include the sample position exchange member 60 in FIG. 6 and FIG. 7 to place or replace the biological samples 20 under different objective lenses 52, the objective lenses 52 can complete acquisition of images of more than two biological samples 20 and including multi-layer slides.

A plurality of movable platforms 40 of the above biological sample image collection devices 100, 200, 300, and 400 are formed in an array distribution on the support 30, and the movable platforms 40 can move in a same direction and at a same speed relative to the array center. Forces acting on the movable platforms 40 and the support 30 offset each other, which can avoid the vibration of the whole support 30 and the biological sample 20 caused by the movement of the movable platform 40, so that the objective lens 52 can obtain accurate fluorescence distribution, and the image sensor 55 can form high-quality fluorescent images of the biological samples 20. The biological sample image collection device of the present disclosure has the advantages of simple structure and high-quality images of biological samples 20.

The present disclosure further provides a gene sequencer, the gene sequencer includes any of the above biological sample image collection devices 100, 200, 300, and 400. As the image quality of the biological sample 20 collected by the biological sample image collection device is improved, the gene sequencer is able to analyze base sequences more rapidly and accurately.

Even though information and advantages of the present embodiments have been set forth in the foregoing description, together with details of the structures and functions of the present embodiments, the disclosure is illustrative only. Changes may be made in detail, especially in matters of shape, size, and arrangement of parts within the principles of the present embodiments to the full extent indicated by the plain meaning of the terms in which the appended claims are expressed.

What is claimed is:

1. A biological sample image collection device comprising:
    a support;
        an optical imaging assembly; comprising:
        a plurality of movable platforms movably connected to the support, and configured for placing biological samples and driving the biological samples to move, the plurality of movable platforms being distributed to form an array on the support, the plurality of movable platforms can move closer to or away from a center of the array simultaneously, forces acting on the support during such movement are balanced in opposition and offset each other, to avoid vibration of the support and the biological samples caused by the movement; and
        an optical imaging assembly configure to collecting images of biological samples on the movable platform when the plurality of movable platforms moves relative to the support platform.

2. The biological sample image collection device as claimed in claim 1, wherein the optical imaging assembly comprises:
    a light source output device configured for outputting light;
    first dichroic mirrors configured for receiving and reflecting the light from the light source output device;
    objective lenses arranged above the movable platform, and configured to focus light reflected by the first dichroic mirror onto the biological sample, and fluorescence from the biological sample is emitted and projected onto the first dichroic mirror;
    the first dichroic mirrors being further configured for transmitting the fluorescence projected by the objective lenses;
    an image sensor configured for forming a fluorescent image of the biological sample; and
    a light guide configured for guiding the fluorescence transmitted by the first dichroic mirror to the image sensor.

3. The biological sample image collection device as claimed in claim 2, wherein the biological sample image collection device comprises a plurality of objective lenses and quantity of the image sensor is one, wherein a photosensitivity range of the image sensor is greater than a sum of imaging ranges of the plurality of objective lenses.

4. The biological sample image collection device as claimed in claim 2, wherein the plurality of objective lenses is arranged above each movable platform, distances between each of the objective lens is equal, and projections of the objective lens divide an image of the biological sample into a plurality of sub images with equal spacing.

5. The biological sample image collection device as claimed in claim 1, further comprising a plurality of objective lenses; and a sample position exchange member,
wherein a focusing distance of each of the objective lenses is at different heights above the movable platform, each of the objective lens is configured to focus light on a slide of a plurality of slides where the biological sample is on, and
wherein when the plurality of movable platforms move relative to the support so that each of the plurality of objective lenses collect fluorescence from a respective one of the plurality of slides, the sample position exchange member changes position of the biological samples under the plurality of objective lenses.

6. The biological sample image collection device as claimed in claim 5, wherein the sample position exchange member is a rotating platform connected to the plurality of movable platforms, the plurality of movable platforms are movably connected to the rotating platform, the rotating platform is arranged on the support, and rotatable around a center of the array on a plane parallel to the movable platforms to exchange positions of the plurality of movable platforms.

7. The biological sample image collection device as claimed in claim 5, wherein the sample position exchange member comprises a manipulator and a plurality of rotating platforms connected to the plurality of movable platforms, the manipulator places the biological sample from one movable platform to another movable platform, and the plurality of rotating platforms drives the movable platform to rotate on a plane parallel to the movable platform.

8. The biological sample image collection device as claimed in claim 1, wherein, a number of the movable platforms is even, all the movable platforms are arranged in a rectangle on the support, each of the even number of movable platforms moves closer to or away from a symmetry axis of the rectangle simultaneously.

9. The biological sample image collection device as claimed in claim 1, wherein the plurality of movable platforms are equally spaced in a circle on the support, angles between two adjacent movable platforms are equal, and all of the movable platforms move closer to or away from a geometric center of the circle simultaneously.

10. A gene sequencer, wherein the gene sequencer comprises the biological sample image collection device as claimed in claim 1.

11. The biological sample image collection device as claimed in claim 3, wherein quantity of the objective lenses is four, two objective lenses are arranged above each of the plurality of movable platforms, a distance between the two objective lenses is half of a length or a width of the biological sample, and one of the objective lenses is facing an edge of the biological sample.

12. The biological sample image collection device as claimed in claim 11, wherein the two objective lenses on one of the movable platforms and the two objective lenses on the other movable platform are centrosymmetric on the center of the array of the plurality of movable platforms.

13. The biological sample image collection device as claimed in claim 2, wherein the light source output device comprises a laser transmitter and an optical splitter, the laser transmitter outputs a laser beam, the optical splitter comprises a laser inlet and a plurality of laser outlets, the optical splitter divides the laser beam from the laser inlet into a plurality of laser beams of equal power, and the plurality of laser outlets output the plurality of laser beams respectively.

14. The biological sample image collection device as claimed in claim 13, wherein the light source output device comprises a plurality of collimators, the plurality of collimators are configured to collimate laser beams from the plurality of laser outlets into parallel light beams, and project the parallel light beams onto first dichroic mirrors, and the first dichroic mirrors project the parallel light beams onto the objective lenses.

15. The biological sample image collection device as claimed in claim 14, wherein a quantity of collimators is the same as a quantity of the objective lenses.

16. The biological sample image collection device as claimed in claim 5, wherein a quantity of the objective lenses is equal to a quantity of layers of a single slide in the biological samples, a focal point of each of the objective lenses is located at a different height above the movable platforms, each of the objective lens is configured to focus on a different layer of a single slide in the biological samples.

17. The biological sample image collection device as claimed in claim 7, wherein the plurality of rotating platforms are respectively placed on sides of the plurality of movable platforms away from the support, and each of the plurality of rotating platforms is configured to receive the biological samples.

* * * * *